United States Patent [19]

Segebart

[11] Patent Number: 4,812,599
[45] Date of Patent: Mar. 14, 1989

[54] INBRED CORN LINE PHV78

[75] Inventor: Robert L. Segebart, Shelbyville, Ill.

[73] Assignee: Pioneer Hi-Bred International, Inc., Johnston, Iowa

[21] Appl. No.: 148,893

[22] Filed: Jan. 27, 1988

[51] Int. Cl.⁴ ............................................. A01H 1/06
[52] U.S. Cl. ................................. 800/1; 47/58; 47/DIG. 1
[58] Field of Search ................. 47/58, DIG. 1; 800/1

[56] References Cited

U.S. PATENT DOCUMENTS 4,654,466  3/1987  Lindsey ........................... 47/58 X
4,731,499  3/1988  Puskaric et al. .................. 47/58 X
4,737,596  4/1988  Seifert et al. ..................... 47/58 X Primary Examiner—James R. Feyrer
Attorney, Agent, or Firm—Saidman, Sterne, Kessler & Goldstein

[57] ABSTRACT

According to the invention, there is provided a novel inbred corn line, designated PHV78. This invention thus relates to the seeds of inbred corn line PHV78, to the plants of inbred corn line PHV78 and to methods for producing a corn plant produced by crossing the inbred line PHV78 with itself or another corn line. This invention further relates to hybrid corn seeds and plants produced by crossing the inbred line PHV78 with another corn line.

12 Claims, No Drawings

INBRED CORN LINE PHV78

FIELD OF THE INVENTION

This invention is in the field of corn breeding, specifically relating to an inbred corn line designated PHV78.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding, five or more generations of selfing and selection is practiced: $F_1 \rightarrow F_2$; $F_2 \rightarrow F_3$; $F_3 \rightarrow F_4$; $F_4 \rightarrow F_5$; etc.

Backcrossing can be used to improve an inbred line. Backcrossing transfers a specific desirable trait from one inbred or source to an inbred that lacks a trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, each of which, although different from each other, bred true and are highly uniform; and (3) crossing the selected bred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeneity of the inbred lines is that essentially all the hybrid plants resulting from a cross between any two inbreds will be genetically uniform. Once the inbreds that give the best hybrid have been identified, the hybrid seed can be reproduced indefinitely as long as the homogeneity of the inbred parent is maintained.

A single-cross hybrid is produced when two inbred lines are crossed to produce the $F_1$ progeny. A double-cross hybrid is produced from four inbred lines crossed in pairs ($A \times B$ and $C \times D$) and then the two $F_1$ hybrids are crossed again ($A \times B$) $\times$ ($C \times D$). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high-yielding corn hybrids that are agronomically sound. The reasons for this goal are obvious: to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated PHV78. This invention thus relates to the seeds of inbred corn line PHV78, to the plants of inbred corn line PHV78 and to methods for producing a corn plant produced by crossing the inbred line PHV78 with itself or another corn line. This invention further relates to hybrid corn seeds and plants produced by crossing the inbred line PHV78 with another corn line.

DEFINITIONS

In the description and examples that follow, a number of terms are used herein. In order to provide a clear and consistent understanding of the specification and claims, including the scope to be given such terms, the following definitions are provided:

Predicted RM. This trait, predicted relative maturity (RM), for a hybrid is based on the harvest moisture of the grain. The relative maturity rating is based on a known set of checks and utilizes standard linear regression analyses and is referred to as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Selection Index. The selection index gives a single measure of the hybrid's worth based on information for up to five traits. A corn breeder may utilize his or her own set of traits for the selection index. One of the traits that is almost always included is yield. The selection index data presented in the tables in the specification represent the mean value averaged across testing stations.

Yield (Bushels/Acre). The yield in bushels/acre is the actual yield of the grain at harvest adjusted to 15.5% moisture.

Percent Yield. The percent yield is the yield obtained for the hybrid in terms of percent of the mean for the experiments in which it was grown.

Moisture. The moisture is the actual percentage moisture of the grain at harvest presented in percent of the mean for the experiments in which the hybrid was grown.

GDU Shed. The GDU shed is the number of growing degree units (GDU) or heat units required for an inbred line or hybrid to reach anthesis or pollen shed from the time of planting. Growing degree units are calculated by the Barger Method, where the heat units for a 24-hour period are:

$$GDU = \frac{(Max. + Min.)}{2} - 50.$$

The highest maximum used is 86° F. and the lowest minimum used is 50° F. For each hybrid it takes a certain number of GDUs to reach various stages of plant development. GDUs are a way of measuring plant maturity. The data is given in percent of the mean for the experiments in which the hybrid was grown.

Stalk Lodging. This is the percentage of plants that do not stalk lodge, i.e., stalk breakage, as measured by either natural lodging or pushing the stalks determining the percentage of plants that break off below the ear. This is a relative rating of a hybrid to other hybrids for standability. The data are given as the percentage of the mean for the experiments in which the hybrid was grown.

Root Lodging. The root lodging is the percentage of plants that do not root lodge; i.e., those that lean from the vertical axis at an approximate 30° angle or greater would be counted as root lodged. The data is given in percentage of mean of the experiments in which the hybrid was grown.

Barren Plants. This is the number of the plants per plot that were not barren (lack ears). The data is converted to percent of the mean for the experiments in which the hybrid was grown.

Stay Green. Stay green is the measure of plant health near the time of black layer formation (physiological maturity). A high score indicates better late-season plant health. The data is given in percentage of mean of the experiments in which the hybrid was grown.

Test Weight. This is the measure of the weight of the grain in pounds for a given volume (bushel) adjusted for percent moisture. The data is given in percentage of mean of the experiments in which the hybrid was grown.

Cob Score. The cob score is a rating of how well the grain is shelled off the cob and how badly the cob is broken up going through the combine. This is given as a 1 to 9 score with 9 being good. A high score indicates that the grain shells off of the cob well, and the cob does not break. The data is given in percentage of mean of the experiments in which the hybrid was grown.

Grain Quality. This a 1 to 9 rating for the general quality of the shelled grain as it is harvested based on the color of the harvested grain, any mold on the grain, and any cracked grain. High scores indicate good grain quality. The data is given in percentage of mean of the experiments in which the hybrid was grown.

Seedling Vigor. This is the visual rating (1 to 9 score) of the amount of vegetative growth after emergence at the seedling stage (approximately five leaves). A higher score indicates better vigor. The data is given in percentage of mean of the experiments in which the hybrid was grown.

Early Stand Count. This is a measure of the stand establishment in the spring and represents the number of plants that emerge on a per-plot basis for the hybrid. The data is given in percentage of mean of the experiments in which the hybrid was grown.

Plant Height. This is a measure of the height of the hybrid from the ground to the tip of the tassel and is measured in inches. The data is given in percentage of mean of the experiments in which the hybrid was grown.

Ear Height. The ear height is a measure from the ground to the ear node attachment and is measured in inches. The data is given in percentage of mean of the experiments in which the hybrid was grown.

Dropped Ears. This is a measure of the number of dropped ears per plot and represents the number of plants that did not drop ears prior to harvest. The data is given in percentage of mean of the experiments in which the hybrid was grown.

Brittle Stalks. This is a measure of the stalk breakage near the time of pollination of the hybrids, and is an indication of whether a hybrid would snap or break at the time of flowering under severe winds. Data are presented as percentage of plants that did not snap. The data is given in percentage of mean of the experiments in which the hybrid was grown.

DETAILED DESCRIPTION OF THE INVENTION

Inbred corn line PHV78 is a yellow dent corn with superior characteristics and provides an excellent parental line in crosses for producing first generation ($F_1$) hybrid corn. Inbred corn line PHV78 was developed from the single cross G42/595 by selfing and using the ear-row pedigree method of breeding. The progenitors of PHV78 are both proprietary inbred lines of Pioneer Hi-Bred International, Incorporated. Selfing and selection were practiced within the above F1 cross for six generations in the development of PHV78 at Shelbyville, Ill. During the development of the line, crosses were made to inbred testers for the purpose of estimating the line's general and specific combining ability and evaluations were run by the Shelbyville Station. The inbred was evaluated further as a line and in numerous crosses by the Shelbyville Research Station and other research station across the Corn Belt. The inbred has proven to have very good combining ability in hybrid combinations as is an excellent male in the production of hybrids. One particular cross showed outstanding performance in research testing across several research stations and was tested extensively.

This inbred is adapted over a wide area of the U.S. Corn Belt and may advantageously be used in hybrids from approximately 117 relative maturity to 130 relative maturity based on the Minnesota Relative Maturity Rating System for harvest moisture of the grain. PHV78 sheds abundant pollen and makes an outstanding male in the production of commercial hybrids. It does not have adequate cold test to be suitable as a female. Relative to Pioneer line G35, PHV78 shed 132% of the experiment mean in pollen weight compared to 106% of the experiment mean for G35 over eight replications. PHV78 has a large tassel that sheds over an extended period of time.

The inbred has shown uniformity and stability for all traits as described in the following variety description information. It has been self-pollinated and ear-rowed a sufficient number of generations with careful attention to uniformity of plant type to ensure homozygosity and phenotypic stability. The line has been increased both by hand and sibbed in isolated fields with continued observation for uniformity. No variant traits have been observed or are expected in PHV78.

Inbred cornline PHVL78 has the following morphological and other charactics (based primarily on data collected at Johnston, Iowa):

PHV78
VARIETY DESCRIPTION INFORMATION

A. Maturity: Zone 6, mid-season or Corn Belt
   INBRED = PHV78
   Heat Unit Shed: 1580
   Heat Unit Silk: 1630
   No. Reps: 33
   Heat Units =

$$\frac{[\text{Max. Temp. } (\leqq 86° \text{ F.}) + \text{Min. Temp. } (\geqq 50° \text{ F.})]^*}{2} - 50$$

B. Plant Characteristics
   Plant height (to tassel tip): 265 cm
   Length of top ear inner node: 7 cm
   Number of ears per stalk: Single
   Ear height (to base of top ear): 95 cm
   Number of tillers: None
   Cytoplasm type: Normal
C. Leaf
   Color: Dark green (B14)
   Angle from stalk: <30°
   Marginal waves: None (Hy)
   Number of leaves (mature plant): 18
   Sheath pubescence: Light (W22)
   Longitudinal creases: Few (OH56A)
   Length (ear node leaf): 82 cm -continued
PHV78
VARIETY DESCRIPTION INFORMATION Width (widest point, ear node leaf): 11 cm
D. Tassel
   Number of lateral branches: 08
   Branch angle from central spike: 30°–40°
   Pollen shed: Heavy
   Peduncle length (top leaf to basal branches): 22 cm
   Anther color: Red - Observed Purplish Red
   Glume color: Green
E. Ear (Husked Ear Data Except When Stated Otherwise)
   Length: 17 cm
   Weight: 120 gm
   Midpoint diameter: 47 mm
   Silk color: Red—observed; deep purplish—red
   Husk extension: Long (8–10 cm beyond ear tip)
   Husk leaf: Long (>15 cm)
   Taper of ear: Average
   Position of shank (dry husks): Upright
   Kernel rows: Number = 15, distinct, straight
   Husk color (fresh): Dark green
   Husk color (dry): Buff—observed very pale yellow
   Shank length: 12 cm
   Shank (no. of internodes): 7
F. Kernel (Dried)
   Size (from ear midpoint):
   Length: 10 mm
   Width: 9 mm
   Thick: 4 mm
   Shape grade (% rounds): <20
   Pericarp color: Colorless
   Aleurone color:
   Homozygous, tan—observed strong orange-yellow
   Endosperm color: Yellow—observed strong orange-yellow
   Endosperm type: Normal starch
   Gm Wt/100 seeds (unsized): 30 gm
G. Cob
   Diameter at midpoint: 29 mm
   Strength: Strong
   Color: Red—observed very dark grayish-reddish brown
H Diseases
   Northern Leaf Blight: Susceptible but some general resistance
   Southern Leaf Blight: Susceptible but some general resistance
   Head Smut: Resistant
   Maize Dwaft Mosaic: Susceptible
   Common Smut: Susceptible but some general resistance
I. Insects
   Corn borer: Susceptible
   Rootworm (western): Susceptible

*If maximum is greater than 86° F., then 86 is used; if minimum is less than 50, then 50 is used. Heat units accumulated daily and cannot be less than 0.

Inbred corn line PHV78 most closely resembles Pioneer line G35 in maturity and plant type characteristics and Pioneer line 595 in ear type, kernel type, and usage characteristics.

This invention is also directed to methods for producing a corn plant by crossing a first parent corn plant with a second parent corn plant wherein the first or second corn plant is the inbred corn plant from the line PHV78. Further both first and second parent corn plants may be from the inbred line PHV78 are part of the invention: selfing, backcrosses, hybrid breeding, and crosses to populations. Any plants produced using inbred corn line PHV78 as a parent are within the scope of this invention. Advantageously, the inbred corn line is used in crosses with other corn varieties to produce firt generation (F₁) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

Tissue culture of corn is described in European patent application, publication No. 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982), at 367–372. Thus, another aspect of this invention is to provide for cells which upon growth and differentiation produce the inbred line PHV78.

USES OF CORN

Corn is used as human food, livestock feed, and as raw material in industry. The food uses of corn, in addition to human consumption of corn kernels, include both products of dry- and wet-milling industries. The principal products of corn dry-milling are grits, meal, and flour. The corn wet-milling industry can provide starch, syrups, and dextrose for food use. Corn oil is recovered from corn germ, which is a by-product of both dry- and wet-milling industries.

hybrid combination. The data collected on inbred corn line PHV78 is presented for the key characteristics and traits.

EXAMPLE 1

The data in Table 1 gives a comparison of PHV78 to G35 crossed to the same tester lines and the hybrids evaluated in the same experiments at the same locations. There were eight Pioneer corn research stations that evaluated crosses with PHV78 and G35 that involved the same tester in the same experiment. G35 is an inbred currently used in commercial production and is a Pioneer proprietary inbred. The results show that PHV78 has 9% yield advantage over G35 for the given testers and is 3% wetter for harvest moisture of the grain. PHV78 is equivalent for stalk lodging resistance but was 5% poorer for root lodging resistance. It has lower test weight in hybrid combination and its hybrids tend to be taller and higher-earred than G35. PHV78 can be utilized in producing hybrids from approximately 117 to 130 relative maturity on the Minnesota Relative Maturity Rating System based on harvest moisture of the grain.

TABLE 1

Comparison of PHV78 and G35 crossed to the same tester lines and the hybrids evaluated in the same experiments. All values are expressed as percent of the experiment mean except Predicted RM, Selection Index and Yield (BU./AC.).

| HYBRID | PREDICTED RM | SELECTION INDEX | YIELD (BU./AC.) | PERCENT YIELD | MOISTURE | GDU SHED | STALK LODGING | ROOT LODGING |
|---|---|---|---|---|---|---|---|---|
| No. Reps. | | 98 | 98 | 98 | 98 | 20 | 82 | 66 |
| PHV78 Crosses | 124 | 104 | 158 | 107 | 102 | 101 | 98 | 95 |
| G35 Crosses | 122 | 97 | 145 | 98 | 99 | 100 | 98 | 100 |
| DIFFERENCE | 2 | 7 | 13 | 9 | 3 | 1 | 0 | 5 |

| HYBRID | BARREN PLANTS | STAY GREEN | TEST WEIGHT | COB SCORE | SEEDLING VIGOR | EARLY STAND COUNT | PLANT HEIGHT | EAR HEIGHT | DROPPED EARS |
|---|---|---|---|---|---|---|---|---|---|
| No. Reps. | 38 | 80 | 96 | 2 | 56 | 62 | 72 | 72 | 42 |
| PHV78 Crosses | 100 | 102 | 98 | 103 | 100 | 99 | 103 | 103 | 101 |
| G35 Crosses | 101 | 108 | 100 | 114 | 105 | 97 | 100 | 99 | 99 |
| DIFFERENCE | 1 | 6 | 2 | 11 | 5 | 2 | 3 | 4 | 2 |

Corn is also used extensively as livestock feed primarily to beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel, to make charcoal.

The seed of inbred corn line PHV78, the plant produced by the inbred seed, the hybrid corn plant produced from the crossing of the inbred, hybrid seed, and various parts of the inbred and hybrid corn plant can be utilized for human food, livestock feed, and as a raw material in the industry.

EXAMPLES

In the examples that follow, the traits and characteristics of inbred corn line PHV78 are given as a line and in

EXAMPLE 2

The data in Table 2 gives the electrophoresis results for PHV78 and its parents G42 and 595. These results are based on 10 plants for each of the inbreds. Any variation for a locus is indicated.

TABLE 2

| Electrophoresis results for PHV78 and its parents G42 and 595 | | | |
|---|---|---|---|
| | Alleles Present | | |
| Locus | PHV78 | G42 | 595 |
| Acp1 | 2 | 2∓ | 4 |
| Adh1 | 4 | 4 | 4 |
| Cat3 | 9 | 9 | 9 |
| Glu1 | N | 7 | 6 |
| Got1 | 4 | 4 | 4 |
| Got2 | 4 | 4 | 4 |
| Got3 | 4 | 4 | 4 |
| Idh1 | 4 | 4 | 4 |
| Idh2 | 6 | 6 | 4* |
| Mdh1 | 1 | 1 | 6 |
| Mdh2 | 3.5 | 3.5 | 6 |
| Mdh3 | 16 | 16 | 16 |
| Mdh4 | 12 | 12 | 12 |
| Mdh5 | 12 | 12 | 12 |
| Mmm | — | — | — |
| Pgm1 | 9 | 9 | 9 |
| Pgm2 | 3 | 4 | 3 |

TABLE 2-continued

Electrophoresis results for PHV78 and its parents G42 and 595

| Locus | Alleles Present | | |
|---|---|---|---|
| | PHV78 | G42 | 595 |
| Pgd1 | 3.8 | 3.8 | 3.8 |
| Pgd2 | 5 | 5 | 5 |
| Phi1 | 4 | 4 | 4 |
| No. plants | 10 | 10 | 10 |

\*Allelic variation of this locus only predominant isozyme form listed.
‡Limited sample number for this locus (2 plants).

Deposit Information

Inbred seeds of PHV78 have been placed on deposit at the American Type Culture Collection (ATCC), Rockville, Md. 20852, under deposit accession number 40413 on Jan. 13, 1988. A Plant Variety Protection Certificate has also been applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn line designated PHV78.
2. A plant or plants of the inbred corn line designated PHV78 of claim 1.
3. Pollen of the plant of claim 2.
4. Seed or seeds of the inbred corn line designated PHV78 of claim 1.
5. An inbred corn plant with the phenotypic physiological and morphologic characteristics of inbred corn line designated PHV78.
6. A method for producing a corn plant comprising crossing a first parent corn plant with a second parent corn plant wherein said first or second parent corn plant is the inbred corn plant having the designation PHV78.
7. The method of claim 6 wherein said first and second parent corn plants are both from the inbred corn line designated PHV78.
8. A first generation ($F_1$) hybrid corn plant produced by crossing a first inbred female corn plant with a second inbred male corn plant wherein said first or second parent corn plant is the inbred corn plant having the designation PHV78.
9. The hybrid corn plant of claim 8 wherein said inbred corn plant having the designation PHV78 is the female parent.
10. The hybrid corn plant of claim 8 wherein said inbred corn plant having the designation PHV78 is the male parent.
11. A method for producing first generation ($F_1$) hybrid corn seed comprising crossing a first inbred parent corn plant with a second inbred parent corn plant, wherein said first or second parent corn plant is the inbred corn plant having the designation PHV78, to produce first generation ($F_1$) hybrid corn seed.
12. A first generation ($F_1$) hybrid corn plant produced by growing said hybrid corn seed of claim 11.

* * * * *